United States Patent
Lennon

(10) Patent No.: US 11,479,776 B2
(45) Date of Patent: Oct. 25, 2022

(54) EXPRESSION SYSTEM

(71) Applicant: Fujifilm Diosynth Biotechnologies UK Limited, Billingham (GB)

(72) Inventor: Christopher Lennon, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 387 days.

(21) Appl. No.: 16/497,102

(22) PCT Filed: Mar. 14, 2018

(86) PCT No.: PCT/GB2018/050649
§ 371 (c)(1),
(2) Date: Sep. 24, 2019

(87) PCT Pub. No.: WO2018/172739
PCT Pub. Date: Sep. 27, 2018

(65) Prior Publication Data
US 2021/0002653 A1    Jan. 7, 2021

(30) Foreign Application Priority Data

Mar. 24, 2017 (GB) .................................... 1704659

(51) Int. Cl.
*C12N 15/73* (2006.01)
*C12N 9/12* (2006.01)
*C12N 15/72* (2006.01)

(52) U.S. Cl.
CPC ........... *C12N 15/73* (2013.01); *C12N 9/1247* (2013.01); *C12N 15/72* (2013.01); *C12Y 207/07006* (2013.01)

(58) Field of Classification Search
None
See application file for complete search history.

(56) References Cited

FOREIGN PATENT DOCUMENTS

| | | |
|---|---|---|
| WO | 2008/139153 A2 | 11/2008 |
| WO | 2008/142028 A1 | 11/2008 |
| WO | 2012/085496 A1 | 6/2012 |
| WO | 2013/178974 A1 | 12/2013 |
| WO | 2016/000961 A1 | 1/2016 |
| WO | 2016/095211 A1 | 6/2016 |

OTHER PUBLICATIONS

Cronan, John E., "Improved plasmid-based system for fully regulated off-to-on gene expression in *Escherichia coli* : Application to production of toxic proteins", PLASMID, vol. 69, No. 1, Jan. 1, 2013 (Jan. 1, 2013), pp. 81-89, XP055472955, us ISSN: 0147-619X, DOI: 10.1016/j.plasmid.2012.09.003 the whole document.

Junhong, Wei et al: "Development and application of a T7 RNA polymerase-dependent expression system for antibiotic production improvement inStreptomyces", Biotechnology Letters, Springer Netherlands, NL, vol. 39, No. 6, Feb. 28, 2017 (Feb. 28, 2017), pp. 857-864, XP036239636, ISSN: 0141-5492, DOI: 10.1007/S10529-017-2309-2 [retrieved on Feb. 28, 2017] the whole document.

Kortmann, Maike et al: "A chromosomally encoded T7 RNA polymerase-dependent gene expression system for C orynebacterium glutamicum : construction and comparative evaluation at the single-cell level: T7 expression system for C. ?gl utami cum", Microbial Biotechnology, vol. 8, No. 2, Dec. 9, 2014 (Dec. 9, 2014), pp. 253-265, XP055472994, GB ISSN: 1751-7915, DOI: 10.1111/1751-7915.12236 the whole document.

*Primary Examiner* — Suzanne M Noakes
*Assistant Examiner* — Jae W Lee
(74) *Attorney, Agent, or Firm* — Banner & Witcoff, Ltd.

(57) ABSTRACT

A protein expression system for use in a prokaryotic host is provided, the expression system comprising: a) an expression cassette comprising a nucleic acid sequence encoding a protein of interest operably linked to a T7 RNA polymerase-dependent promoter; and b) an expression cassette comprising a nucleic acid sequence encoding T7 RNA polymerase operably linked to a host polymerase-dependent λ phage promoter and a single perfect palindrome operator sequence; wherein the expression cassette for T7 RNA polymerase is located on the chromosome of a host cell.

14 Claims, No Drawings

Specification includes a Sequence Listing.

EXPRESSION SYSTEM

RELATED APPLICATIONS

This application is a National Stage Application under 35 U.S.C. 371 of co-pending PCT application PCT/GB2018/050649 designating the United States and filed Mar. 14, 2018; which claims the benefit of GB application number 1704659.0 and filed Mar. 24, 2017 each of which are hereby incorporated by reference in their entireties.

The present invention concerns methods and systems for expressing proteins, and specifically methods and systems employing the T7 promoter.

The T7 promoter system is well known for use in the expression of proteins. However, whilst the T7 promoter is recognised as being effective in its ability to express proteins, T7 based systems suffer from certain drawbacks. Operation of the T7 system requires phage polymerase which is commonly provided by inserting a λDE3 prophage expressing the required phage polymerase into the *Escherichia coli* host strain to create lysogenic host strains. The phage polymerase can also be delivered to the cell by infection with a specialised λ transducing phage that carries the gene for the phage polymerase (e.g. T7 RNA polymerase). The λDE3 prophage lacks the genetic elements required for the excision of the prophage to form lytic phage particles. However, λDE3 lysogenic host strains have been shown to release phage particles and thus have the potential to cause undesirable infections in fermentation plants. Indeed, the use of λDE3 strains is not permitted by certain fermentation plant operators.

Tabor and Richardson (Proc Natl Acad Sci (1985) 82:1074-1078) showed that an operable expression system could be constructed by expressing T7 RNA polymerase from a λPL promoter on one plasmid, and linking a Gene of Interest ("GOI") to the T7 promoter on another plasmid. However, this system gave high uninduced levels of GOI. Mertens et al (Bio/Technology (1995)13:175-179) demonstrated that the system of Tabor and Richardson (supra) as configured is inherently unstable due to the high background expression. The solution they proposed was to add transcription terminators in between the promoter and the T7 RNA polymerase. It was shown that combining this with a temperature inducible λPL promoter led to tight repression. However, this required induction using elevated temperature, which they acknowledged did not allow the flexibility of expression at lower temperatures that may increase product solubility. When an alternative IPTG inducible promoter was used, this was found to give leaky expression, which led to long-term instability. One other problem with systems such as those proposed by Tabor and Richardson, and by Mertens et al, is that when the system is induced then there will be a high level of T7 RNA polymerase expression, which due to its capacity to synthesise large amounts of RNA, which can then be translated into protein, leads to a large metabolic burden on the cell. This places limitations on the use of such systems in fermentation processes, as the induction period can not last very long because the cells stop growing shortly after induction.

There have been a number of reports of alternatives to the LacUV5 promoter, as used in DE3, for expression of T7 RNA polymerase. These include:

a) the use of the arabinose promoter, but this still gives detectable basal levels of expression (see for example, Wycuf (2000) Anal Biochem 277:67-73, Chao et al (2002) Biotechnol Prog 18:394-400);

b) a salt inducible expression system (U.S. Pat. No. 5,830,690), for which there is evidence of instability (Bhandari P and Gowrishankar J. J Bact 1997 179:4403-6);

c) a rhamnose inducible system (Promega Notes (2006) 94:27-30), but this is highly strain specific, and requires high concentrations of an expensive inducer; and d) the gal promoter, which showed a relatively high uninduced level of expression (Menzel) and Gramajo (2004) Biotechnol Prog 20:1263-6).

WO2008139153 discloses a protein expression system wherein an expression cassette for T7 RNA polymerase is operably linked to a λpL promoter and at least two perfect palindrome operator sequences.

It remains desirable to identify further T7-based expression systems.

According to a first aspect of the present invention, there is provided a protein expression system for use in a prokaryotic host comprising:

a) an expression cassette comprising a nucleic acid sequence encoding a protein of interest operably linked to a T7 RNA polymerase-dependent promoter; and b) an expression cassette comprising a nucleic acid sequence encoding T7 RNA polymerase operably linked to a host polymerase-dependent λ phage promoter and a single perfect palindrome operator sequence;

wherein the expression cassette for T7 RNA polymerase is located on the chromosome of a host cell.

The expression cassette for the T7 RNA polymerase can be incorporated into the host cell chromosome using methods known in the art, such as homologous recombination, site-specific recombination or transposon-mediated gene transposition. In some embodiments, the T7 RNA polymerase expression cassette is incorporated into different locations in different hosts, and hosts having particularly active expression are selected.

T7 RNA polymerase-dependent promoter systems employed in the expression system are preferably single T7 promoters. Examples of such promoters are well known in the art, and include those disclosed by Studier and Moffat, J. Mol. Biol. 189:113-130 (1986), incorporated herein by reference. Most preferably, the T7 RNA polymerase-dependent promoter system employed is a T7 gene 10 promoter.

Operator sequences which may be employed as perfect palindrome operator sequences in the expression system according to the present invention include lac, gal, deo and gln. In many embodiments, the operator sequence is located downstream of the host cell polymerase-dependent promoter. Preferred operator sequences are lac operators, and most preferably operators having the nucleic acid sequences GGAATTGTGAGCGCTCACAATTCC (SEQ ID NO 1) or AATTGTGAGCGCTCACAATT (SEQ ID NO. 2). In preferred embodiments, an operator sequence overlaps with the transcriptional start point.

The T7 RNA polymerase-dependent promoter is commonly employed under the control of at least one operator sequence, which may be palindromic or non-palindromic. Examples of operator sequences which can be employed are well known in the art and include lac, gal, deo, gln, raf, rha, araC, fru and mel. When two operators are employed to control the T7 RNA polymerase-dependent promoter, the operator sequences are preferably spaced to maximise control of the promoter. In many embodiments, the spacing is from 85 to 150 base pairs apart, such as from 90 to 126 base pairs apart, for example 91 or 92 base pairs apart. In preferred embodiments, one operator, preferably a perfect palindrome operator, is located upstream of the promoter, and one operator, preferably a perfect palindrome operator, is located downstream of the promoter. In certain embodiments, an operator sequence, especially a perfect palindrome operator sequence, overlaps with the transcriptional start point.

In certain embodiments, it is preferred that the operator controlling the T7 RNA polymerase-dependent promoter system is induced by the same inducer as the perfect palindrome operator sequence controlling the host cell polymerase-dependent promoter. For example, when the host cell polymerase-dependent promoter is controlled by perfect palindromic lac, gal, deo or gln, the T7 RNA polymerase-dependent promoter system is advantageously controlled by the corresponding perfect palindromic, or non-palindromic, lac, gal, deo or gln operator.

It will be recognised that the operators are commonly employed with an appropriate repressor sequence. Repressor sequences produce repressor protein, for example lacI gene sequence when using the lac operators. Other lac repressor sequences may also be used, for example the lacI$^Q$ sequence can be used to increase the level of lac repressor protein. The repressor sequence may also be provided by the host cell genome or by using an additional compatible plasmid. In many embodiments, the repressor sequence selected for the operators controlling the host cell polymerase-dependent promoter serve as repressor sequences for the operator sequence controlling the T7 RNA polymerase-dependent promoter.

The T7 RNA polymerase-dependent promoter of the expression system may be integrated into the host cell genome, but is preferably comprised within extrachromosomal elements such as plasmids.

Plasmids or expression vectors comprising the expression system of the present invention can be assembled by methods known in the art. The plasmid typically also comprises one or more of the following: a selectable marker, for example a sequence conferring antibiotic resistance, a cer stability sequence and an expression cassette. The expression system may also incorporate a signal sequence if secretion of the desired protein is required.

Expression may be induced by the addition of an inducer such as isopropyl-β-D-1-thiogalactopyranoside (IPTG), analogues of IPTG such as isobutyl-C-galactoside (IBCG), lactose or melibiose. Other inducers may be used and are described more fully elsewhere (e.g. see The Operon, eds Miller and Renznikoff (1978)). Inducers may be used individually or in combination. The construction of appropriate plasmids or expression vectors will be apparent to the scientist of ordinary skill.

The expression system of the present invention can be employed to express proteins in prokaryotic host cells, and especially in microorganisms. As used herein, "proteins" refers generally to polypeptides typically having more than about 10 amino acids.

Examples of prokaryotic cells include bacterial cells, for example gram-negative bacterial cells, including *E. coli, Salmonella typhimurium, Serratia marcescens* and *Pseudomonas aeruginosa*, and gram-positive bacterial cells including *Bacillus subtilis*. Preferred host cells are enterobacteriacae, preferably *E coli*, and especially B or K12 strains thereof. In certain embodiments, the host cell is engineered to be deficient in at least one native protease. In many preferred embodiments, the host cell is an ompT- *E. coli* strain, especially a W3110 *E. coli* strain.

Examples of host polymerase-dependent λ phage promoters include λpL, λpR and λcl, preferably λpL.

In many highly preferred embodiments, the expression systems comprises an *E coli*, and especially B or K12 strains thereof, engineered to be deficient in at least one native protease, especially an ompT- *E. coli* strain, most especially a W3110 *E. coli* strain, wherein the promoter is a λpL promoter.

The expression system of the present invention is advantageously employed for the manufacture of proteins, especially recombinant or heterologous proteins, by culturing recombinant cells. For the expression of proteins, it will be recognised that the promoter and operator sequence are operably linked to a nucleic acid, most commonly DNA, encoding a protein to be expressed.

Accordingly, the present invention also provides a method for the production of a protein which comprises expressing an expression system comprising:

a) an expression cassette comprising a nucleic acid sequence encoding a protein of interest operably linked to a T7 RNA polymerase-dependent promoter; and b) an expression cassette comprising a nucleic acid sequence encoding T7 RNA polymerase operably linked to a host polymerase-dependent λ phage promoter and a single perfect palindrome operator sequence;

wherein the expression cassette for T7 RNA polymerase is located on the chromosome of a host cell.

Preferred features for the method of production of the production are as set out in respect of the expression system according to the first aspect of the present invention.

The expression system is expressed by methods well known in the art for the cells employed. Preferred expression methods include culturing the recombinant cells in growth medium, especially by fermentation, and then recovering the expressed protein. The term "growth medium" refers to a nutrient medium used for growing the recombinant cells. In many embodiments, a nutrient solution is employed. Suitable growth media for given recombinant cells are well known in the art.

In many embodiments, the protein recovery comprises one or more of filtration, centrifugation, diafiltration, ion-exchange chromatography, affinity chromatography, such as Protein A affinity chromatography, Hydrophobic Interaction Chromatography (HIC), Gel Filtration and HPLC.

The present invention is illustrated without limitation by the following examples.

CONSTRUCTION OF EXPRESSION STRAIN CLD1362

The starting strain for the construction of expression strain CLD1362 was a W3110 (CGSC4474) strain with a clean in frame deletion of the ompT Open Reading Frame designated as CLD1040. To introduce the T7 RNA Polymerase expression cassette onto the chromosome a synthetic DNA molecule was synthesised.

The T7 RNA polymerase gene (DNA sequence obtained from Genbank entry GU071091.1) was synthesised. A λpL promoter cassette comprising twin perfect palindromic lac operators, one located upstream and one downstream of the promoter, and T7 gene 10 translation initiation region was placed at the 5'- end of the T7 RNA polymerase gene with an NcoI site flanking the upstream palindromic operator. On each side of the promoter cassette and polymerase construct 700 bp of *E. coli* genomic DNA sequence flanking the chromosomal insertion point was placed. The sequence is given in Seq ID No.3 below, where the *E coli* genomic DNA is singleunderlined, the λpL promoter is doubleunderlined, the operators are in bold, and the transcriptional start point is the bold underlined A.

SEQ ID No. 3

<u>GCGGCCGCCTTACAAAAAAGGGAGAGGATGCATATTTTAAATATCACTG</u>
<u>AAGTGAACAGTTTATTTCCGTTATTAATAGAAATGGAGAAATAAATAGG</u>
<u>CGTATTCTACAATTGCGACAAAAACAACGATATTAATCAGTTTATGACT</u>
<u>GATTTGCTGTACTTTATTCTCTTTCATTGGTACTTCCTCGCTTTAAAAA</u>
<u>AGAGTGCACTTCGTAAGTGCCCTTATATAAATAACGAGTTTGGTCAACC</u>
<u>AATTTTTGACATGTATCACAAATTTGAATAGATGTATTACATCAACTA</u>
<u>TCTTTTATTGCACCAACGTCATTGATATATGTCGCCTGAAGTCAGTTCC</u>
<u>GGGAATGAGTCTGATCTCAAGACTGGCCCAGTCCGGGCGTTGATTGGTG</u>
<u>CTGAGGAGCATATCGCATCTCATCATAATGTCGTATCTCCTGGGGTGTT</u>
<u>ATACAAGATATCGTTGTTGGTGACCTGGGAGAGGAATTGAGTTCTATTA</u>
<u>AACCGTCAACTATGCCGGATACATACTGGATTACACTGCAGGCACGCCT</u>
<u>TATGAGAGAACGTGCCGCAGTGACGGGTTAATTATCTGAAAGAATTTGT</u>
<u>GAGGCTGTATCGGTTACTCATTGATTTGATAGTTTTACTCTCGGGAGAA</u>
<u>TAATAGATATTTAATCCATTAACGGAAACCAGCCAGTTCCTTTCGATGC</u>
<u>CTGAATTTGATCCCATAGTTTA</u>CCATGGTGGGAATTGTGAGCGCTCACA
ATTCCAAGAACAATCCTGCACCCATGGT<u>CTCTGGCGGTGTTGACATAAA</u>
<u>TACCACTGGCGGTGATACTGAGC</u>GGAATTGTGAGCGCTCACAATTCCCC
ACTAGAAATAATTTTGTTTAACTTAAGAAGGAGATATACATATGAACA
CGATTAACATCGCTAAGAACGACTTCTCTGACATCGAACTGGCTGCTAT
CCCGTTCAACACTCTGGCTGACCATTACGGTGAGCGTTTAGCTCGCGAA
CAGTTGGCCCTTGAGCATGAGTCTTACGAGATGGGTGAAGCACGCTTCC
GCAAGATGTTTGAGCGTCAACTTAAAGCTGGTGAGGTTGCGGATAACGC
TGCCGCCAAGCCTCTCATCACTACCCTACTCCCTAAGATGATTGCACGC
ATCAACGACTGGTTTGAGGAAGTGAAAGCTAAGCGCGGCAAGCGCCCGA
CAGCCTTCCAGTTCCTGCAAGAAATCAAGCCGGAAGCCGTAGCGTACAT
CACCATTAAGACCACTCTGGCTTGCCTAACCAGTGCTGACAATACAACC
GTTCAGGCTGTAGCAAGCGCAATCGGTCGGGCCATTGAGGACGAGGCTC
GCTTCGGTCGTATCCGTGACCTTGAAGCTAAGCACTTCAAGAAAAACGT
TGAGGAACAACTCAACAAGCGCGTAGGGCACGTCTACAAGAAAGCATTT
ATGCAAGTTGTCGAGGCTGACATGCTCTCTAAGGGTCTACTCGGTGGCG
AGGCGTGGTCTTCGTGGCATAAGGAAGACTCTATTCATGTAGGAGTACG
CTGCATCGAGATGCTCATTGAGTCAACCGGAATGGTTAGCTTACACCGC
CAAAATGCTGGCGTAGTAGGTCAAGACTCTGAGACTATCGAACTCGCAC
CTGAATACGCTGAGGCTATCGCAACCCGTGCAGGTGCGCTGGCTGGCAT
CTCTCCGATGTTCCAACCTTGCGTAGTTCCTCCTAAGCCGTGGACTGGC
ATTACTGGTGGTGGCTATTGGGCTAACGGTCGTCGTCCTCTGGCGCTGG
TGCGTACTCACAGTAAGAAAGCACTGATGCGCTACGAAGACGTTTACAT
GCCTGAGGTGTACAAAGCGATTAACATTGCGCAAAACACCGCATGGAAA
ATCAACAAGAAAGTCCTAGCGGTCGCCAACGTAATCACCAAGTGGAAGC
ATTGTCCGGTCGAGGACATCCCTGCGATTGAGCGTGAAGAACTCCCGAT

GAAACCGGAAGACATCGACATGAATCCTGAGGCTCTCACCGCGTGGAAA
CGTGCTGCCGCTGCTGTGTACCGCAAGGACAAGGCTCGCAAGTCTCGCC
GTATCAGCCTTGAGTTCATGCTTGAGCAAGCCAATAAGTTTGCTAACCA
TAAGGCCATCTGGTTCCCTTACAACATGGACTGGCGCGGTCGTGTTTAC
GCTGTGTCAATGTTCAACCCGCAAGGTAACGATATGACCAAAGGACTGC
TTACGCTGGCGAAAGGTAAACCAATCGGTAAGGAAGGTTACTACTGGCT
GAAAATCCACGGTGCAAACTGTGCGGGTGTCGATAAGGTTCCGTTCCCT
GAGCGCATCAAGTTCATTGAGGAAAACCACGAGAACATCATGGCTTGCG
CTAAGTCTCCACTGGAGAACACTTGGTGGGCTGAGCAAGATTCTCCGTT
CTGCTTCCTTGCGTTCTGCTTTGAGTACGCTGGGGTACAGCACCACGGC
CTGAGCTATAACTGCTCCCTTCCGCTGGCGTTTGACGGGTCTTGCTCTG
GCATCCAGCACTTCTCCGCGATGCTCCGAGATGAGGTAGGTGGTCGCGC
GGTTAACTTGCTTCCTAGTGAAACCGTTCAGGACATCTACGGGATTGTT
GCTAAGAAAGTCAACGAGATTCTACAAGCAGACGCAATCAATGGGACCG
ATAACGAAGTAGTTACCGTGACCGATGAGAACACTGGTGAAATCTCTGA
GAAAGTCAAGCTGGGCACTAAGGCACTGGCTGGTCAATGGCTGGCTTAC
GGTGTTACTCGCAGTGTGACTAAGCGTTCAGTCATGACGCTGGCTTACG
GGTCCAAAGAGTTCGGCTTCCGTCAACAAGTGCTGGAAGATACCATTCA
GCCAGCTATTGATTCCGGCAAGGGTCTGATGTTCACTCAGCCGAATCAG
GCTGCTGGATACATGGCTAAGCTGATTTGGGAATCTGTGAGCGTGACGG
TGGTAGCTGCGGTTGAAGCAATGAACTGGCTTAAGTCTGCTGCTAAGCT
GCTGGCTGCTGAGGTCAAAGATAAGAAGACTGGAGAGATTCTTCGCAAG
CGTTGCGCTGTGCATTGGGTAACTCCTGATGGTTTCCCTGTGTGGCAGG
AATACAAGAAGCCTATTCAGACGCGCTTGAACCTGATGTTCCTCGGTCA
GTTCCGCTTACAGCCTACCATTAACACCAACAAAGATAGCGAGATTGAT
GCACACAAACAGGAGTCTGGTATCGCTCCTAACTTTGTACACAGCCAAG
ACGGTAGCCACCTTCGTAAGACTGTAGTGTGGGCACACGAGAAGTACGG
AATCGAATCTTTTGCACTGATTCACGACTCCTTCGGTACCATTCCGGCT
GACGCTGCGAACCTGTTCAAAGCAGTGCGCGAAACTATGGTTGACACTT
ATGAGTCTTGTGATGTACTGGCTGATTTCTACGACCAGTTCGCTGACCA
GTTGCACGAGTCTCAATTGGACAAAATGCCAGCACTTCCGGCTAAAGGT
AACTTGAACCTCCGTGACATCTTAGAGTCGGACTTCGCGTTCGCGTAAC
TCGAGGTCCGG<u>AATGGTTAATTCATGAACAAGTTGTGTTATCGTTCATG</u>
<u>AGAAGCATAACGTAAAGGGAAAAGCTCGATTAGACGGCAGAATTTGTCA</u>
<u>GGGGTTATGAACGAAATTCATAAATCTGTTTGAGTGTTGCGATGGGTAG</u>
<u>TGCAAGTTCGATATCTCCGCAATTTACAGTCCGATGAAGGAAAATGAAT</u>
<u>ATCCATAAAAAATATATTGGTTTATCCTGGCATATATACCTATTTCGAC</u>
<u>GTATTTCCAATAGTTTTAATTAAAGGCAGGTCATTGTTATTCACTCTGA</u>
<u>ATAGTGAATTATTCACTGTCCGCAGAGTAAGAAAATAAACTTAGGTATC</u>
<u>TATTTAATGACTTGCACAAAAAGCTAAATTTTCCCCCATAAATAAAAAT</u>
<u>ATAATCCCGCGCCCAACCACCTGATGAGTGGCTATAGGCACTGGATATA</u>

-continued

TTAGGTGGCGGTGCACTTTCTTACATAAAGGTATTTCCTTTTCTGCGGA

AAAGGAAATCGGGAAATCCCCGGTTTTTCTGACAAGCAGACGCCATTAT

TTGTGTCTGCCTATGTTCGTTAATTCGTTCATCAGGAAATTATCTCAAT

GTCACATTATAAAACAGGTCATAAACAACCACGATTTCGTTATTCAGTT

CTGGCCCGCTGCGTGGCGTGGGCAAATATCTCTGTTCAGGTTCTTTTTC

CACTCGCTGTCACCTTTACCGTCGAC

The integration cassette was cloned as NotI/SalI into pAVE1050, a pSC101 based plasmid with a temperature sensitive replicon to make pAVE1079. The resulting plasmid was digested with NcoI to remove the operator sequence upstream of the promoter, and re-ligated to become pAVE1160.

pAVE1160 was separately transformed into CLD1040. Once the plasmid was established the strains were spread onto LB+ Chloramphenicol an incubated at a non-permissive temperature. The resultant colonies were returned to a permissive temperature and subcultured three times before plating onto LB sucrose counter-selection plates. Resultant colonies were picked onto LB & LB+ Chloramphenicol plates. Chloramphenicol sensitive colonies were screened by PCR to confirm presence of the integrated transgene. A single positive colony was purified and maintained as glycerol stocks at −70° C. named as CLD1362.

Construction of Test Plasmid

The Super Folder GFP gene sequence was obtained from *Nat Biotechnol.* 2006 January;24(1):79-88. Epub 2005 Dec. 20. Engineering and characterization of a superfolder green fluorescent protein. Pedeclacq J D, Cabantous S, Tran T, Terwilliger T C, Waldo G S. A gene coding for this protein was synthesised with optimisation for expression in *E.coli*. This gene was cloned as an NdeI/XhoI fragment into a pZT7#3.3 expression vector as described in patent application WO99/05297. Recombinant plasmids were screened by restriction digest and confirmed by sequencing. The resultant plasmid was named pAVE1030.

Construction of pAVE1231 (Comparative)

A T7A3 Promoter Cassette (Seq ID No.4) was synthesised and cloned by NcoI/NdeI to pAVE1079 to create pAVE1231.

SEQ ID No. 4
CCATGGAAACAAAACGGTTGACAACATGAAGTAAACACGGTACGATGTA

CCGGAATTGTGAGCGCTCACAATTCCCCACTAGAAATAATTTTGTTTAA

CTTTAAGAAGGAGATATACATATG

Construction of CLD1392 (Control)

The plasmid pAVE1030 was transformed into CLD1040. The resultant recombinant strain (named CLD1392) was purified and maintained as glycerol stocks at −70° C.

Construction of CLD1394

The plasmid pAVE1030 was transformed into CLD1362. The resultant recombinant strain (named CLD1394) was purified and maintained as glycerol stocks at −70° C.

Construction of CLD1395 (Comparative)

The plasmid pAVE1030 was transformed into BL21 (λDE3) (Novagen™ catalogue no. 69450-3). The resultant recombinant strain (CLD1395) was purified and maintained as glycerol stocks at −70° C.

Integration of pAVE1231 into CLD1040 (Comparative)

Two attempts were made to integrate the pAVE1231 plasmid into the CLD1040 chromosome. Neither attempt yielded any clones with the T7 RNA polymerase expression cassette integrated into the chromosome.

Microwell Plate Expression of sfGFP

A vial of each CLD1392, CLD1394 and CLD1395 was removed from the −70° C. freezer and allowed to thaw. 10 μL of the thawed glycerol stock was inoculated into 5 mL of veggie Luria Broth (vLB 5 g/L Yeast Extract (BD), 10 g/L Select Soytone (BD), and 5 g/L sodium chloride supplemented with tetracycline (10 μg/mL). Cultures were incubated at 37° C. in an orbital shaker for 16 h. 20 μL of this culture was inoculated into 4 wells on a 24 deep well plate containing 2 mL of vLB (composition as described above). The plate was incubated at 37° C., at 200 rpm in an orbital shaker. Three hours post inoculation the plate was removed from the shaker. 20 μsamples were removed from each well for Flow Cytometry analysis. Then three wells were induced with IPTG (isopropyl-β.-D-1-thiogalactopyranoside) to final concentration of 0.005 mM, 0.05 mM and 0.5 mM respectively. The fourth well was left un-induced to monitor basal expression. The incubation was continued, under the conditions described above. Further samples were taken for Flow Cytometry analysis at three hours and twenty two hours post induction to measure the accumulation of sfGFP.

Flow cytometry analysis was performed on a BD Accuri C6 Flow Cytometer using the FL1-A detector. Collection settings were maximum 10000 events, 2 mins with medium fluidics. The accumulation level of sfGFP was determined using densitometry scanning of Colloidal Blue stain SDS-PAGE gels of whole cell lysates of the sampled bacteria. The results are shown in Table 1

TABLE 1

Median FL1-A & Percentage Total Cell Protein levels

| Strain/IPTG concentration | FL1-A Readings | | | % Total Cell Protein |
|---|---|---|---|---|
| | Induction | 3 Hours Post Induction | 22 Hours Post Induction | |
| CLD1392 0.0 mM | 363 | 927 | 1345 | n/a |
| CLD1392 0.005 mM | 360 | 1433 | 2331 | n/a |
| CLD1392 0.05 mM | 363 | 2326 | 2443 | n/a |
| CLD1392 0.5 mM | 372 | 2275 | 2793 | 0% |
| CLD1394 0.0 mM | 721 | 2226 | 3761 | n/a |
| CLD1394 0.005 mM | 745 | 5162 | 275726 | n/a |
| CLD1394 0.05 mM | 736 | 331601 | 1055893 | n/a |
| CLD1394 0.5 mM | 710 | 1053011 | 1172348 | 14.10% |
| CLD1395 0.0 mM | 80969 | 28922.5 | 564308 | n/a |
| CLD1395 0.005 mM | 87024 | 50983 | 950420 | n/a |
| CLD1395 0.05 mM | 88529 | 984706 | 1357173 | n/a |
| CLD1395 0.5 mM | 82382 | 2809975 | 853902 | 13.20% |

The data shows that delivering T7 RNA polymerase from a λpL promoter and single palindromic lac operator integrated onto the *E.coli* chromosome (CLD1394) gives similar levels of fluorescent intensity and sfGFP accumulation as the use of a BL21 λDE3 strain (CLD1395) after 22 hours of induction. Surprisingly, the FL1-A levels of the BL21 λDE3 strain CLD1395 at the point immediately prior to induction were in excess of 100 times higher than those for CLD1394. CLD1394 at induction had only twice the FL1-A levels of the control strain CLD1392, which did not contain a T7 RNA Polymerase gene. Additionally, CLD1395 exhibited poor stability overnight, as evidenced by the decline in FL1-A levels at 0.5 mM IPTG between 3 and 22 hours. This demonstrates that the CLD1394 host strain (according to the present invention) is less leaky in terms of recombinant protein production than those utilising λDE3, whilst being capable of induction to produce the same levels of target protein expression. This is particularly surprising when it is considered that the CLD1394 strain has a T7 RNA polymerase gene operably linked to the integrated promoter whereas CLD1395 would be expected to have impeded translation of the T7 RNA polymerase gene due to the LacZα fragment open reading frame between the promoter and the T7 RNA Polymerase gene on the λDE3 construct.

Fermentation Evaluation

Fermentation inocula for the strains CLD1394 and CLD1395 were raised by adding 50 μl of glycerol stock of each of the strains described below to a 500 mL baffled shake flask containing 200 mL of Luria Broth (LB, 5 g/L yeast extract (Oxoid), 10 g/L tryptone (Oxoid), and 5 g/L sodium chloride) supplemented with 15 μg/ml of tetracycline. Inocula were grown for 12 h at 37° C. in a shaker-incubator with an agitation of 200 rpm. 0.75 ml shake flask inoculum was used to inoculate a 250 mL working volume fermenter containing 150 mL of defined glycerol batch growth medium. Fermentations were carried out under the operating conditions described below. Temperature was controlled at 37° C. and pH at 6.7, controlled by automatic addition of 35% (w/v) ammonium hydroxide. The dissolved oxygen tension (dOT) set point was 30% of air saturation and was controlled by automatic adjustment of the fermenter stirrer speed, from a minimum of 500 rpm up to a maximum of 4500 rpm, and automatic supplementation of oxygen to the inlet gas stream. Airflow to the fermenter vessel was 1.0 v/v/m throughout. Pressure in the fermenter was maintained between 50 and 200 mbar.

Fermentations were performed in batch mode until depletion of the carbon source (i.e. glycerol) which occurred ca. 10 h post inoculation and was characterized by a sharp rise in dOT. Fed-batch fermentation was initiated at the point of carbon source exhaustion by the addition of a glycerol/ammonium sulphate feed at a capped feed rate. Induction was carried out by addition of IPTG to a final concentration of 0.0 mM, 0.1 mM, 0.25 mM or 0.5 mM 1.5 hours after depletion. The fed-batch phase was continued for 12 h post induction. Samples were taken to determine Fluorescence levels by Flow Cytometry (at induction) and Green Fluorescent Protein (GFP) accumulation (% TCP) at harvest, 12 hours post induction (Colloidal Blue stained SDS-PAGE gels).

The Flow Cytometry results are summarised in Table 2, below.

TABLE 2

| Strain | Count | Median Fluorescence |
|---|---|---|
| CLD1394 0.0 mM | 431 | 543 |
| CLD1394 0.1 mM | 539 | 544 |
| CLD1394 0.25 mM | 408 | 518 |
| CLD1394 0.5 mM | 466 | 475 |
| CLD1394 (mean) | 461 | 520 |
| CLD1395 0.0 mM | 1,051 | 550 |
| CLD1395 0.1 mM | 711 | 710 |
| CLD1395 0.25 mM | 691 | 571 |
| CLD1395 0.5 mM | 884 | 562 |
| CLD1395 (mean) | 834 | 598 |

The data in Table 2 shows that at induction the four CLD1394 bioreactors have only 55% the numbers of fluorescent events compared to the four CLD1395 bioreactors. The median fluorescence level is only 86% of that seen in the CLD1395. This shows the CLD1394 strain has much lower basal expression levels in the defined fermentation media, replicating the effect seen in the complex media used in the microwell plates.

Table 3 shows the accumulation of GFP at the end of fermentation for the strains as percentage total cellular protein.

TABLE 3

| Strain | % Total Cell Protein |
|---|---|
| CLD1394 0.0 mM | 0 |
| CLD1394 0.1 mM | 18.0 |
| CLD1394 0.25 mM | 17.3 |
| CLD1394 0.5 mM | 17.8 |
| CLD1395 0.0 mM | 0 |
| CLD1395 0.1 mM | 13.9 |
| CLD1395 0.25 mM | 15.9 |
| CLD1395 0.5 mM | 16.0 |

Table 2 shows that despite CLD1394 having lower basal expression at induction than CLD1395 the final accumulation of test protein is as high, or higher than the CLD1395 strain after normalising for optical density.

The data clearly demonstrate the utility of the systems for the manufacture of heterologous proteins. Lower basal expression and higher induced productivity for the expression system of the present invention were obtained.

The invention claimed is:

1. A protein expression system comprising:
   a) an expression cassette comprising a nucleic acid sequence encoding a protein of interest operably linked to a T7 RNA polymerase-dependent promoter; and
   b) an expression cassette comprising a nucleic acid sequence encoding T7 RNA polymerase operably linked to a host polymerase-dependent λ phage promoter and a single perfect palindrome operator sequence;
   wherein the expression cassette for T7 RNA polymerase is located on the chromosome of a host cell, and wherein the operator operably linked to the host polymerase-dependent λ phage promoter overlaps the transcriptional start point.

2. The protein expression system according to claim 1, wherein the host polymerase-dependent λ phage promoter is a λ pL promoter.

3. The protein expression system according to claim 1, wherein the host cell is *E. coli*.

4. The protein expression system according to claim 1, wherein the T7 RNA polymerase-dependent promoter is under the control of two perfect palindrome operator sequences.

5. The protein expression system according to claim 4, wherein one perfect palindrome operator is located upstream of the T7 RNA polymerase-dependent promoter, and one perfect palindrome operator, is located downstream of the T7 RNA polymerase-dependent promoter.

6. The protein expression system according to claim 4, wherein the operator controlling the T7 RNA polymerase-dependent promoter and the operator operably linked to the host cell polymerase-dependent λ phage promoter are induced by the same inducer.

7. The protein expression system according to claim 1, wherein the operator operably linked to the host cell polymerase-dependent λ phage promoter is a lac operator.

8. The protein expression system according to claim 1, wherein the single perfect palindrome operator sequence is either GGAATTGTGAGCGCTCACAATTCC (SEQ ID NO: 1) or AATTGTGAGCGCTCACAATT (SEQ ID NO: 2).

9. The protein expression system according to claim 1, further comprising an expression cassette for a protein operably linked to the T7 RNA polymerase-dependent promoter.

10. A process for the preparation of a protein, which comprises expressing the protein expression system according to claim 1.

11. The process according to claim 10, which further comprises recovering the protein.

12. A method for the production of a protein which comprises expressing, in a prokaryotic host, an expression system comprising:
   a) an expression cassette comprising a nucleic acid sequence encoding a protein of interest operably linked to a T7 RNA polymerase-dependent promoter; and
   b) an expression cassette comprising a nucleic acid sequence encoding T7 RNA polymerase operably linked to a host polymerase-dependent λ phage promoter and a single perfect palindrome operator sequence;
   wherein the expression cassette for T7 RNA polymerase is located on the chromosome of a host cell, and wherein the operator operably linked to the host polymerase-dependent λ phage promoter overlaps the transcriptional start point.

13. The method according to claim 12, wherein the prokaryotic host is *E. coli*, the T7 RNA polymerase-dependent promoter is under the control of two perfect palindrome operator sequences, one perfect palindrome operator being located upstream of the T7 RNA polymerase-dependent promoter, and one perfect palindrome operator being located downstream of the T7 RNA polymerase-dependent promoter, and the host polymerase-dependent λ phage promoter is a λ pL promoter.

14. The method according to claim 13, wherein the two perfect palindrome operator sequences are selected from the group consisting of GGAATTGTGAGCGCTCACAATTCC (SEQ ID NO: 1) and AATTGTGAGCGCTCACAATT (SEQ ID NO: 2).

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: operator sequence

<400> SEQUENCE: 1
ggaattgtga gcgctcacaa ttcc                                              24

<210> SEQ ID NO 2
<211> LENGTH: 20
<212> TYPE: DNA
<213> ORGANISM: Artificial Sequence
<220> FEATURE:
<223> OTHER INFORMATION: operator sequence

<400> SEQUENCE: 2
aattgtgagc gctcacaatt                                                   20

<210> SEQ ID NO 3
<211> LENGTH: 4240
<212> TYPE: DNA
<213> ORGANISM: Artificial Sequence
<220> FEATURE:
<223> OTHER INFORMATION: DNA construct used in Examples

<400> SEQUENCE: 3
gcggccgcct tacaaaaaag ggagaggatg catattttaa atatcactga agtgaacagt        60
ttatttccgt tattaataga aatggagaaa taataggcg tattctacaa ttgcgacaaa        120
aacaacgata ttaatcagtt tatgactgat ttgctgtact ttattctctt tcattggtac       180
ttcctcgctt taaaaagag tgcacttcgt aagtgcccctt atataaataa cgagtttggt       240
caaccaattt tttgacatgt atcacaaatt tgaatagatg tattacatca actatctttt       300
attgcaccaa cgtcattgat atatgtcgcc tgaagtcagt tccgggaatg agtctgatct       360
caagactggc ccagtccggg cgttgattgg tgctgaggag catatcgcat ctcatcataa       420
tgtcgtatct cctggggtgt tatacaagat atcgttgttg gtgacctggg agaggaattg       480
agttctatta accgtcaac tatgccggat acatactgga ttacactgca ggcacgcctt        540
atgagagaac gtgccgcagt gacgggttaa ttatctgaaa gaatttgtga ggctgtatcg       600
gttactcatt gatttgatag ttttactctc gggagaataa tagatatta atccattaac       660 ggaaaccagc cagttccttt cgatgcctga atttgatccc atagtttacc atggtgggaa       720
ttgtgagcgc tcacaattcc aagaacaatc ctgcacccat ggtctctggc ggtgttgaca       780
taaataccac tggcggtgat actgagcgga attgtgagcg ctcacaattc cccactagaa       840
ataattttgt ttaactttaa gaaggagata tacatatgaa cacgattaac atcgctaaga       900 acgcttctc tgcatcgaa ctggctgcta tcccgttcaa cactctggct gaccattacg        960
gtgagcgttt agctcgcgaa cagttggccc ttgagcatga gtcttacgag atgggtgaag      1020
cacgcttccg caagatgttt gagcgtcaac ttaaagctgg tgaggttgcg ataacgctg       1080 ccgccaagcc tctcatcact accctactcc ctaagatgat tgcacgcatc aacgactggt      1140
ttgaggaagt gaaagctaag cgcggcaagc gcccgacagc cttccagttc ctgcaagaaa      1200
tcaagccgga agccgtagcg tacatcacca ttaagaccac tctggcttgc ctaaccagtg      1260
ctgacaatac aaccgttcag gctgtagcaa gcgcaatcgg tcgggccatt gaggacgagg      1320
ctcgcttcgg tcgtatccgt gaccttgaag ctaagcactt caagaaaaac gttgaggaac      1380
aactcaacaa gcgcgtaggg cacgtctaca agaaagcatt tatgcaagtt gtcgaggctg      1440
acatgctctc taagggtcta ctcggtggcg aggcgtggtc ttcgtggcat aaggaagact      1500
ctattcatgt aggagtacgc tgcatcgaga tgctcattga gtcaaccgga atggttagct      1560

-continued

```
tacaccgcca aaatgctggc gtagtaggtc aagactctga gactatcgaa ctcgcacctg    1620
aatacgctga ggctatcgca acccgtgcag gtgcgctggc tggcatctct ccgatgttcc    1680
aaccttgcgt agttcctcct aagccgtgga ctggcattac tggtggtggc tattgggcta    1740
acggtcgtcg tcctctggcg ctggtgcgta ctcacagtaa gaaagcactg atgcgctacg    1800
aagacgttta catgcctgag gtgtacaaag cgattaacat tgcgcaaaac accgcatgga    1860
aaatcaacaa gaaagtccta gcggtcgcca acgtaatcac caagtggaag cattgtccgg    1920
tcgaggacat ccctgcgatt gagcgtgaag aactcccgat gaaaccggaa gacatcgaca    1980
tgaatcctga ggctctcacc gcgtggaaac gtgctgccgc tgctgtgtac cgcaaggaca    2040
aggctcgcaa gtctcgccgt atcagccttg agttcatgct tgagcaagcc aataagtttg    2100
ctaaccataa ggccatctgg ttcccttaca acatggactg gcgcggtcgt gtttacgctg    2160
tgtcaatgtt caacccgcaa ggtaacgata tgaccaaagg actgcttacg ctggcgaaag    2220
gtaaaccaat cggtaaggaa ggttactact ggctgaaaat ccacggtgca aactgtgcgg    2280
gtgtcgataa ggttccgttc cctgagcgca tcaagttcat tgaggaaaac cacgagaaca    2340
tcatggcttg cgctaagtct ccactggaga acacttggtg ggctgagcaa gattctccgt    2400
tctgcttcct tgcgttctgc tttgagtacg ctggggtaca gcaccacggc ctgagctata    2460
actgctccct tccgctggcg tttgacgggt cttgctctgg catccagcac ttctccgcga    2520
tgctccgaga tgaggtaggt ggtcgcgcgg ttaacttgct tcctagtgaa accgttcagg    2580
acatctacgg gattgttgct aagaaagtca acgagattct acaagcagac gcaatcaatg    2640
ggaccgataa cgaagtagtt accgtgaccg atgagaacac tggtgaaatc tctgagaaag    2700
tcaagctggg cactaaggca ctggctggtc aatggctggc ttacggtgtt actcgcagtg    2760
tgactaagcg ttcagtcatg acgctggctt acggtccaa agagttcggc ttccgtcaac    2820
aagtgctgga agataccatt cagccagcta ttgattccgg caagggtctg atgttcactc    2880
agccgaatca ggctgctgga tacatggcta agctgatttg ggaatctgtg agcgtgacgg    2940
tggtagctgc ggttgaagca atgaactggc ttaagtctgc tgctaagctg ctggctgctg    3000
aggtcaaaga taagaagact ggagagattc ttcgcaagcg ttgcgctgtg cattgggtaa    3060
ctcctgatgg tttccctgtg tggcaggaat acaagaagcc tattcagacg cgcttgaacc    3120
tgatgttcct cggtcagttc cgcttacagc ctaccattaa caccaacaaa gatagcgaga    3180
ttgatgcaca caaacaggag tctggtatcg ctcctaactt tgtacacagc caagacggta    3240
gccaccttcg taagactgta gtgtgggcac acgagaagta cggaatcgaa tcttttgcac    3300
tgattcacga ctccttcggt accattccgg ctgacgctgc gaacctgttc aaagcagtgc    3360
gcgaaactat ggttgacact tatgagtctt gtgatgtact ggctgatttc tacgaccagt    3420
tcgctgacca gttgcacgag tctcaattgg acaaaatgcc agcacttccg gctaaaggta    3480
acttgaacct ccgtgacatc ttagagtcgg acttcgcgtt cgcgtaactc gaggtccgga    3540
atggttaatt catgaacaag ttgtgttatc gttcatgaga agcataacgt aaagggaaaa    3600
gctcgattag acggcagaat ttgtcagggg ttatgaacga aattcataaa tctgtttgag    3660
tgttgcgatg ggtagtgcaa gttcgatatc tccgcaattt acagtccgat gaaggaaaat    3720
gaatatccat aaaaaatata ttggtttatc ctggcatata tacctatttc gacgtatttc    3780
caatagtttt aattaaaggc aggtcattgt tattcactct gaatagtgaa ttattcactg    3840
tccgcagagt aagaaatata acttaggtat ctatttaatg acttgcacaa aaagctaaat    3900
tttcccccat aaataaaaat ataatcccgc gcccaaccac ctgatgagtg gctataggca    3960
```

```
ctggatatat taggtggcgg tgcactttct tacataaagg tatttccttt tctgcggaaa      4020
aggaaatcgg gaaatccccg gttttctga caagcagacg ccattatttg tgtctgccta       4080
tgttcgttaa ttcgttcatc aggaaattat ctcaatgtca cattataaaa caggtcataa      4140
acaaccacga tttcgttatt cagttctggc ccgctgcgtg gcgtgggcaa atatctctgt      4200
tcaggttctt tttccactcg ctgtcacctt taccgtcgac                            4240

<210> SEQ ID NO 4
<211> LENGTH: 122
<212> TYPE: DNA
<213> ORGANISM: Artificial Sequence
<220> FEATURE:
<223> OTHER INFORMATION: T7A3 prooter used in Comparative Example

<400> SEQUENCE: 4
ccatggaaac aaaacggttg acaacatgaa gtaaacacgg tacgatgtac cggaattgtg        60
agcgctcaca attccccact agaaataatt ttgtttaact ttaagaagga gatatacata       120
tg                                                                      122
```